United States Patent
Laffont et al.

(10) Patent No.: US 7,184,135 B2
(45) Date of Patent: Feb. 27, 2007

(54) REFRACTOMETER WITH BLAZED BRAGG GRATINGS

(75) Inventors: Guillaume Laffont, Gif-sur-Yvette (FR); Pierre Ferdinand, Houilles (FR)

(73) Assignee: Commissariat a l'Energie Atomique, Paris (FR)

( * ) Notice: Subject to any disclaimer, the term of this patent is extended or adjusted under 35 U.S.C. 154(b) by 151 days.

(21) Appl. No.: 09/926,511

(22) PCT Filed: Oct. 2, 2001

(86) PCT No.: PCT/IB01/01814

§ 371 (c)(1),
(2), (4) Date: Nov. 11, 2002

(87) PCT Pub. No.: WO02/44697

PCT Pub. Date: Jun. 6, 2002

(65) Prior Publication Data

US 2003/0098971 A1 May 29, 2003

(30) Foreign Application Priority Data

Sep. 24, 2000 (FR) .................. 00 12430

(51) Int. Cl.
*G01N 21/41* (2006.01)

(52) U.S. Cl. ...................... 356/128
(58) Field of Classification Search ........ 356/128–137; 250/227.18, 227.21, 227.16, 227.14, 227.19
See application file for complete search history.

(56) References Cited

U.S. PATENT DOCUMENTS

| 5,073,024 A | 12/1991 | Valette et al. |
| 5,380,995 A | 1/1995 | Clark et al. |
| 5,493,390 A * | 2/1996 | Varasi et al. ............ 356/32 |
| 5,638,473 A * | 6/1997 | Byron ..................... 385/37 |
| 6,363,180 B1 * | 3/2002 | Yamate et al. ............ 385/12 |

(Continued)

FOREIGN PATENT DOCUMENTS

ES 2 150 386 11/2000

(Continued)

OTHER PUBLICATIONS

W. Ecke et al.: "Optical fiber grating sensor network for monitoring refractive index and temperature distributions in fluids" Optical Diagnostics for Fluids/Heat/Combustion and Photomechanics for Solids, Denver, CO, USA, vol. 3783, pp. 176-183 Jul. 21- Jul. 23, 1999.
V. Bhatia et al.: "Comparison of optical fiber long-period and bragg grating sensors" Proceedings of the SPIE, SPIE, Bellingham, VA, US, vol. 2718, pp. 110-121 Feb. 26, 1996.

*Primary Examiner*—Michael P. Stafira
(74) *Attorney, Agent, or Firm*—Oblon, Spivak, McClelland, Maier & Neustadt, P.C.

(57) ABSTRACT

A refractometer with blazed Bragg gratings. In order to measure the refractive index of a medium, for example a liquid or a gas, the refractometer includes a waveguide having a blazed Bragg grating, the spectral response of which depends on the refractive index of the medium and a light source in order to make this light interact with the grating. Further, spectral analysis of the light which has interacted with the grating is performed, the spectrum provided by the spectral analysis is recovered, and, from the recovered spectrum, the spectral response of the grating is correlated with one value of the refractive index of the medium.

11 Claims, 3 Drawing Sheets

U.S. PATENT DOCUMENTS 6,427,041 B1 * 7/2002 Strasser et al. ............... 385/37
6,597,822 B1 * 7/2003 Moslehi et al. ............... 385/13
2002/0036767 A1 * 3/2002 Blondel et al. ............ 356/73.1

FOREIGN PATENT DOCUMENTS

FR 2814810 * 4/2002

* cited by examiner

REFRACTOMETER WITH BLAZED BRAGG GRATINGS

DESCRIPTION

1. Technical Field

The present invention relates to a refractometer, that is to say a system for measuring refractive indices.

It is applicable especially to measuring the refractive index of a liquid or of a gas or of any other product or chemical compound which is contact with a waveguide, in particular deposited on this waveguide. The latter may for example be an optical fibre.

The refractometer comprises one or more Bragg grating transducers formed on such a waveguide.

2. Description of the Prior Art

A Bragg grating, photo-inscribed in an optical fibre, is a periodic structure formed by modulating the refractive index of the core of the fibre.

This structure behaves in practice like a mirror for a very narrow spectral band around a characteristic wavelength $\lambda_B$ (wavelength for which there is phase matching between the multiple reflections within the grating) and remains transparent for all other wavelengths. This is because, since the multiple waves reflected at these other wavelengths are not in phase, they interfere destructively and are therefore transmitted because of the conservation of energy.

The characteristic wavelength, called the "Bragg wavelength", is defined by the equation $\lambda_B = 2 \times n_{eff} \times \Lambda$ where $\Lambda$ is the pitch of the Bragg grating (about 0.5 μm for a standard grating) and $n_{eff}$ is the effective index of the fundamental guided mode incident on the grating.

Long Period Fibre Bragg Gratings (LPFG) are also formed by a periodic modulation of the refractive index of the core of a generally monomode optical fibre. However, the value of the period $\Lambda$ of this modulation is then typically greater than 100 μm.

When light from a broadband source is injected into a fibre containing such a grating, a number of resonant bands are observed, with widths at half maximum which are much greater than that of a conventional Bragg grating (several nanometres instead of a few hundred picometres). Each of these resonant bands corresponds to a coupling between the guided light wave incident on the grating and a mode called "cladding mode" which is copropagating (also called codirectional), this mode being propagated in the same direction as the incident wave.

The energy contained in these modes decreases rapidly during propagation through the fibre, because of the high losses at the interface between the optical cladding and the coating protecting this fibre.

Since the coupling takes place to the codirectional modes, the resonant bands appear only in the form of absorption bands on the transmission spectrum such that no energy is observed in reflection.

The wavelengths for which the phenomenon of coupling to the cladding modes occurs depend on the period $\Lambda$ of the long-period grating, on the amplitude of the photo-induced modulation, denoted $\Delta n$, and on the opto-geometrical characteristics of the optical fibre. They are given by the condition called phase matching, as follows:

$$\beta_{01} - \beta_{clad} = \frac{2\pi}{\Lambda} \quad (1)$$

where $\beta_{01}$ and $\beta_{clad}$ represent the propagation constants of the fundamental guided mode and of a cladding mode, respectively. This equation can be rewritten substituting the effective indices of the modes:

$$\frac{2 \cdot \pi}{\lambda_{grat}} \cdot n_{01}^{eff} - \frac{2 \cdot \pi}{\lambda_{grat}} \cdot n_{clad}^{eff} = \frac{2 \cdot \pi}{\Lambda} \quad (2)$$

$$\lambda_{grat} = (n_{01}^{eff} - n_{clad}^{eff}) \cdot \Lambda \quad (3)$$

where $\lambda_{grat}$ denotes the central wavelength of the resonant band.

The Bragg gratings, called "blazed, tilted or slanted fibre Bragg gratings", result from a photo-induced modulation of the index, the period of which is also about 0.5 μm. However, this modulation has the specific feature of being blazed, with respect to the longitudinal axis of the optical fibre, by an angle $\theta$ which is called the "blaze angle".

This periodicity and the blaze of the index modulation constitute the two key parameters making it possible to explain the very particular spectral response of these components and the considerable differences between the latter and the conventional Bragg gratings together with the long period Bragg gratings.

FIG. 1 schematically represents a blazed Bragg grating 2 inscribed in the core 4 of an optical fibre 6, the optical cladding of which has the reference 7. A guided mode 8 incident on the grating can be coupled either to a discrete set of cladding modes 10 which are counter-propagating, or to what is called a continuum of radiative modes 12 or both to these cladding modes and this continuum of radiative modes.

The discretization of the coupling to the counter-propagating cladding modes is conditioned by the finite transverse dimensions of the optical fibre cladding. From the spectral point of view, the result thereof is a succession of resonant bands which have widths at half maximum similar to those of a standard Bragg grating (width at half maximum of about 200 pm) and are typically spaced apart by about one nanometre.

These resonant bands are present over a narrow spectral range (a few tens of nanometres) which depends on the blaze angle and on the opto-geometrical characteristics of the fibre and of the grating (modulation period and amplitude). Coupling to the radiative modes can only take place if the cladding of the optical fibre is very large compared to the wavelength.

This configuration can be simulated by using an index-matching liquid which is deposited around the fibre and the refractive index of which is virtually identical to that of the optical cladding.

FIG. 2 shows a transmission spectrum of a blazed Bragg grating, which is 8 mm long with a blaze angle of 16°, when this grating is in air with a refractive index $n_{ext}$ of of 1.0 (curve I) and when it is in an index matching liquid for which the value of $n_{ext}$ is 1.43 at 1550 nm (curve II). The wavelength X (in nm) is plotted on the x-axis and the normalized transmission TN on the y-axis. Where coupling is to the cladding modes, coupling to the families of modes called $LP_{0n}$ and $LP_{1n}$ is mainly observed.

For the blazed gratings, the phase-matching condition giving the value of the various resonant wavelengths takes the form:

$$\lambda_{grat} = (n_{01}^{eff} + n_{clad}^{eff}) \cdot \frac{\Lambda}{\cos\theta} \quad (4)$$

where $\lambda_{grat}$ denotes a resonant wavelength, $\Lambda$ the modulation period, $\theta$ the blaze angle, $n_{01}^{eff}$ and $n_{clad}^{eff}$ the effective index of the guided mode and the effective index of a cladding mode, respectively. The + symbol arises from the fact that counter-propagating modes rather than codirectional modes are involved.

Intrinsic optical fibre sensors (OFS), sensors for which one or more optical properties of the fibre depend directly, for example, on chemical and/or biochemical phenomena which it is desired to determine, are considered below. The optical fibre then constitutes the transducer element of the sensor.

In particular, evanescent-wave intrinsic sensors and surface plasmon sensors are known.

Devices using standard Bragg gratings which are photo-inscribed in the monomode optical fibres for the purpose of applications to refractometry, are also known.

Furthermore, refractometry systems which use long period Bragg gratings are known. For such gratings, the resonant wavelength associated with a given cladding mode depends on the refractive index of the medium which is located beyond the optical cladding of the fibre in which these gratings are formed. Any change in this refractive index results in a shift of the resonant wavelength.

The known sensors or systems, mentioned above, have drawbacks.

With regard to evanescent-wave sensors, the following will mainly be noted:

the ageing and the deterioration of the sensitive part of such sensors, for example formed by the mediating agent deposited on the optical fibre of these sensors, which necessitates frequent recalibrations thereof, the difficulty in developing methods to compensate for the degradation in the performance of these sensors, the intensity measurement on which the use of the latter is based and which is therefore sensitive to any intensity fluctuation of the associated light source and to modification in the conditions for injecting the light into the fibre, hence a deterioration in the resolution and in the accuracy of measurements, and the need for mechanically or chemically removing the cladding from the optical fibre in order to have sufficient access to the evanescent field, which is a complex operation, is difficult to control and which weakens the optical fibre.

Among the drawbacks of surface plasmon sensors, let us mention:

the difficulty in forming all-fibre miniaturized systems since systems using such sensors generally employ bulky components around an architecture which is difficult to convert into an industrial system, and the need to control perfectly the profile (mainly the thickness) of the metal layer used in such sensors and the attachment of this layer.

Among the drawbacks of devices using standard Bragg gratings, there are problems similar to those presented by the evanescent wave sensors, namely:

the need to chemically or mechanically attack the cladding of the optical fibre at the measuring Bragg grating, a selectivity problem, since the Bragg peak is sensitive to parameters other than the index of the external medium (for example temperature and strain), which requires the use of compensation and correction techniques employing, for example, reference sensors, the relative weakness of the final measuring head, the difficulty in producing the transducer, requiring the optical cladding to be attacked, and relatively low sensitivity.

With regard to refractometry systems using the long period Bragg gratings, the main drawbacks are as follows:

great sensitivity of the long period grating resonant to parameters other than the refractive index (for example temperature and deformations), hence the need to use compensation and correction techniques, high non-linearity of the transducer sensitivity, extremely limited multiplexing capacities since a very sensitive sensor monopolizes a large spectral range, of at least 100 nm, and large width of the resonant band, making it difficult to determine the peak of the latter accurately.

SUMMARY OF THE INVENTION

The aim of the present invention is to overcome the abovementioned drawbacks.

The object of the invention is a system for measuring the refractive index of at least one medium, this system being characterized in that it comprises:

a waveguide comprising at least one transducer formed, in the part of the waveguide brought into contact with the medium, by a blazed Bragg grating, the spectral response of which depends on the refractive index of the medium by means of energy coupling between the guided mode and cladding modes and/or a continuum of radiative modes, a light source optically coupled to the waveguide in order to direct this light therein and to make it interact with the grating, spectral analysis means provided to analyse the light which has interacted with the grating and to provide a spectrum corresponding to this grating, acquisition means provided to recover this spectrum, and electronic processing means provided to correlate, from the spectrum thus recovered, the spectral response of the grating with a value of the refractive index of the medium and to provide this value.

According to a first preferred embodiment of the system which is the subject of the invention, the electronic processing means are provided in order to determine the lower and upper envelope curves of the normalized spectrum and the normalized area between these two curves.

The waveguide, for example an optical fibre, may comprise a single blazed Bragg grating or, in contrast, a plurality of such gratings. In the latter case, the spectral analysis means are provided in order to analyse the light which has interacted with the gratings and to provide the spectra corresponding respectively to these gratings; the acquisition means are provided in order to demultiplex, in an optical or digital manner, the spectra thus provided and to discriminate the respective spectral responses of the gratings and the electronic processing means are provided in order to correlate the spectral response of each grating with the value of the refractive index of the medium corresponding to this grating.

In all cases, the light source may be a broadband source. However, it is also possible to use a narrow spectrum source, the wavelength of which can be tuned, and the spectral analysis means may then comprise a single photodetector.

According to a first particular embodiment of the system which is the subject of the invention, the light source is optically coupled to a first end of the waveguide and the spectral analysis means are optically coupled to a second end of this waveguide, for the purpose of measuring the refractive index by transmission.

According to a second particular embodiment, the light source and the spectral analysis means are optically coupled to a first end of the waveguide and means of reflecting the light are provided at the second end of the waveguide, for the purpose of measuring the refractive index by reflection.

BRIEF DESCRIPTION OF THE DRAWINGS

The present invention will be better understood on reading the description of exemplary embodiments given below, purely by way of example and in no way limiting, with reference to the appended drawings in which.

DETAILED SUMMARY OF PARTICULAR EMBODIMENTS

First of all, let us consider the transducers used in the present invention to measure refractive indices, that is to say blazed Bragg gratings, for example photo-inscribed in the core of optical fibres, and let us start by studying the spectral sensitivity of such a grating with any modification of the refractive index by an external medium with which the waveguide comprising this grating is in contact.

Let us therefore consider an optical fibre, or any other waveguide, in which a blazed Bragg grating has been inscribed. This grating may have been formed according to any one of the known photo-inscription methods, for example the "phase mask" or "Lloyd mirror" techniques.

In the rest of the present description, the numerical values are given only by way of illustration and are not limiting in any case. They relate to a monomode optical fibre having the following characteristics: core and cladding indices having the values of 1.462 and 1.457, respectively, at 1550 nm, core and cladding radii having the values of 4.125 μm and 62.5 μm, respectively.

When light is injected into such a waveguide, it interacts with the blazed grating. It is then coupled to a number of cladding modes. This coupling only takes place for incident wavelengths which comply with a condition called phase matching between the guided mode and any one of the cladding modes.

This condition is only complied with by a discrete number of wavelengths, which results from the existence of discrete resonant bands.

The location and the amplitude of these various spectral resonants depend not only on the opto-geometrical parameters of the guide (especially indices and dimensions of the core and of the optical cladding) but also on the refractive index of the external medium, a medium which surrounds the optical cladding of the guide.

When this refractive index is modified, the various resonant bands shift spectrally and change amplitude.

Let us take the case of a grating having a blaze angle θ of 16°. When the refractive index $n_{ext}$ of the external medium changes from 1.0 (index of air) to 1.3, the spectral resonant bands shift towards long wavelengths, on average by 200 pm, without significant change in their attenuation.

In contrast, when $n_{ext}$ goes from 1.3 to 1.43, a phenomenon of progressive disappearance of the resonant bands is observed together with a slight spectral shift, until obtaining a perfectly smooth and continuous loss spectrum.

Figure 1:
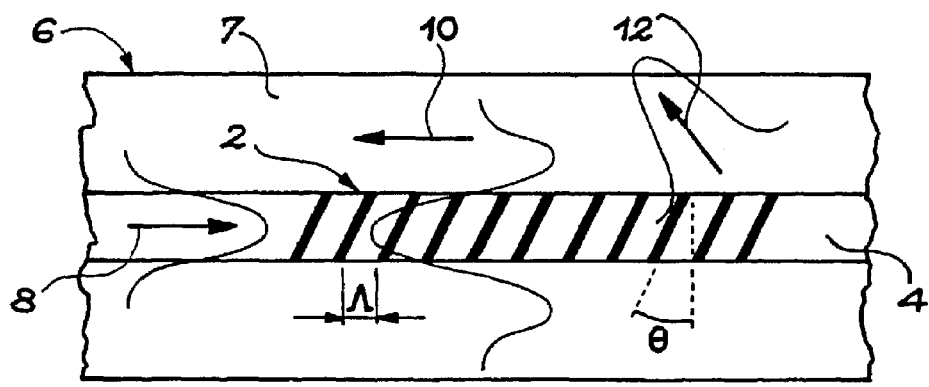
FIG. 1 is a schematic view of a blazed Bragg grating and has already been described.
Figure 2:
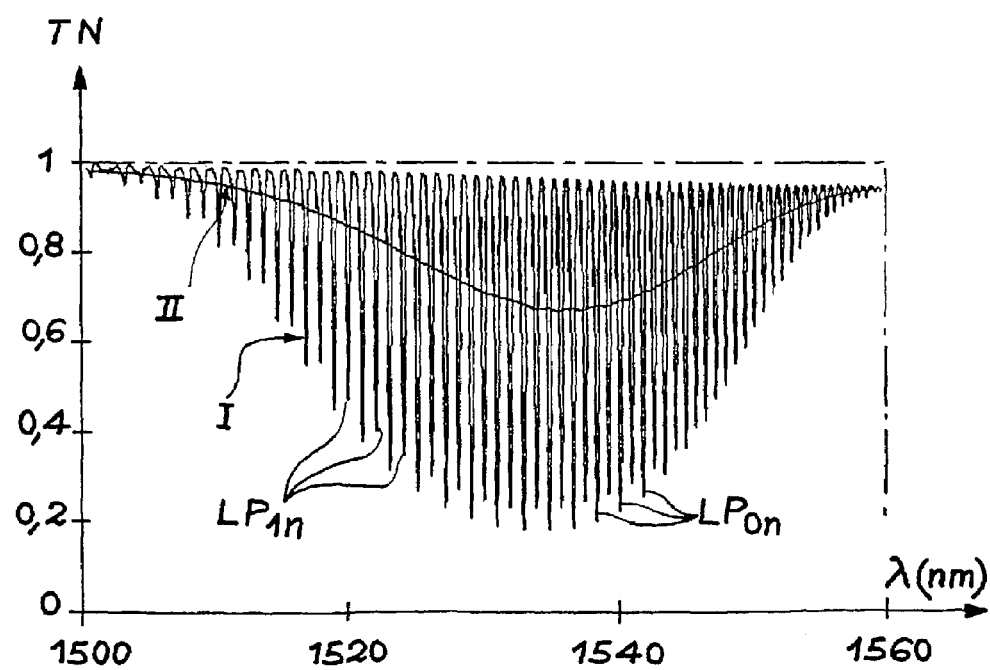
FIG. 2 shows a transmission spectrum of a blazed Bragg grating and has already been described.

FIG. 2 already described shows the spectrum of such a grating in air and in a medium of index 1.43.

The phenomenon mentioned above may be explained as follows. With each resonant wavelength $\lambda_i$ it is possible to associate a cladding mode of effective index $n_{\mathit{eff},i}$ which decreases with $\lambda_i$.

When the refractive index of the external medium increases until reaching the value $n_{\mathit{eff},i}$, the cladding mode is progressively less guided because of the decrease in the overlap integral between the guided core mode and this cladding mode. The result of this is a reduction in the amplitude of the corresponding resonant band.

When $n_{ext}$ is equal to $n_{\mathit{eff},i}$, the cladding mode is no longer guided; however, coupling takes place with the continuum of radiative modes.

In the present invention, in order to profit from this phenomenon, an analysis technique is used which consists in determining the lower envelope $\epsilon_l$ of the normalized loss spectrum of the blazed Bragg transducer grating (passing through the maxima of the spectrum) and the upper envelope $\epsilon_u$ of the same spectrum (passing through the minima of the spectrum) then the normalized area A between these two envelopes.

The determination of the envelopes takes place, for example, through the determination of the troughs and peaks of the various resonant bands or, which is equivalent, through determining the minima and maxima of the transmission spectrum.

These minima and maxima can be located by a direct method of detecting extrema or using a derivation operation, leading to a derived curve, then detecting the zeros of this curve. Finally, the lower envelope is obtained by interpolation of the set of maxima, for example using spline functions.

The upper envelope is also obtained by interpolation, using such functions, of the set of the minima.

Instead of measuring the variation in the refractive index of the external medium in the form of a shift in wavelength of a resonant band, the change in the normalized area A is followed, which is defined as follows:

$$A = \frac{\int_{\lambda_{min}}^{\lambda_{max}} [\epsilon_u(\lambda) - \epsilon_l(\lambda)] d\lambda}{\int_{\lambda_{min}}^{\lambda_{max}} [\epsilon_u^{n_{ref}}(\lambda) - \epsilon_l^{n_{ref}}(\lambda)] d\lambda} \quad (5)$$

where $\epsilon_u(\lambda)$ and $\epsilon_l(\lambda)$ are respectively the upper and lower envelopes of the normalized loss spectrum of the blazed Bragg transducer grating, $\lambda_{min}$ and $\lambda_{max}$ are the limits of the spectral window comprising all the spectral resonances of the grating (here, 1495 nm and 1575 nm respectively).

$\epsilon_u^{n_{\mathit{eff}}}$ and $\epsilon_l^{n_{\mathit{eff}}}$ are two envelopes which are taken as a reference and which correspond to the blazed grating spectrum placed in an external medium of refractive index beyond which only a spectral shift can be observed (here, $n_{ref} = n_{ext} = 1.296$).

When the refractive index of the external medium increases beyond 1.3, the progressive smoothing of the spectrum is equivalent to progressively bringing the two envelopes together and, consequently, to a decrease in the normalized area A.

The benefit of the definition of A above is to make the measurement independent of any fluctuation in intensity of the source which emits the light injected into the waveguide. This is important for any industrial application of the invention.

Let us specify that the resolution and the repeatability of the measurements made with the blazed Bragg gratings and the analysis technique described above have a value of about $10^{-5}$.

In the invention, at least one blazed Bragg grating is therefore used in order to measure the refractive index $n_{ext}$ of a medium in contact with the optical fibre in which this grating is photo-inscribed. The sensitivity of such a grating to the refractive index of the medium results in a progressive smoothing of the set of resonant bands present in the transmission spectrum when $n_{ext}$ increases. The method of analysing this spectrum may consist in following the change in the area between the envelope passing through the minima of the resonant bands and the envelope passing through the maxima of these bands. It is thus possible to carry out measurements with a resolution and a repeatability of about $10^{-5}$. Moreover, it is possible to adapt the dynamics of measurements by altering the blaze angle θ. A value of about 16° for the latter makes it possible to cover the refractive index range from 1.32 to 1.42 (values given for a wavelength of 1550 nm).

In the foregoing, the transmission spectra of blazed gratings have been used in order to carry out refractometry. In fact, it is possible to work in reflection. In order to do this, a mirror sending the light back in the reverse direction is placed at the end of the fibre.

In this case, the light, which is propagated through the core of the fibre, interacts twice with the transducer grating. The resulting spectrum, which can be observed at the input by means of an optical coupler, corresponds simply to the square of the transmission spectrum.

The analysis method explained above for operating in transmission is strictly identical when operating in reflection, except that all the processing is carried out on the square of the transmission spectrum.

Next, examples of a system for measuring the refractive index according to the invention, which uses at least one blazed Bragg grating operating in transmission, will be considered. It is necessary to obtain the spectra from this transducer grating. Given the width of the resonant bands and their spectral spacing, it is therefore necessary to obtain these spectra with sufficient resolution if it is desired to optimize the resolution of the refractive index measurements.

In order to be able to detect index variations of about $10^{-5}$, it is necessary to acquire the spectra with wavelength pitches of about 10 picometres. With lower-resolution spectra (for example with pitches of a few tens of picometres) the resolution of the measurements would not be as good.

Let us specify that the spectral range that it is desired to analyse may go from a few nanometres to several tens of nanometres. This mainly depends on the dynamics of measurement that it is desired to obtain.

Figure 3:
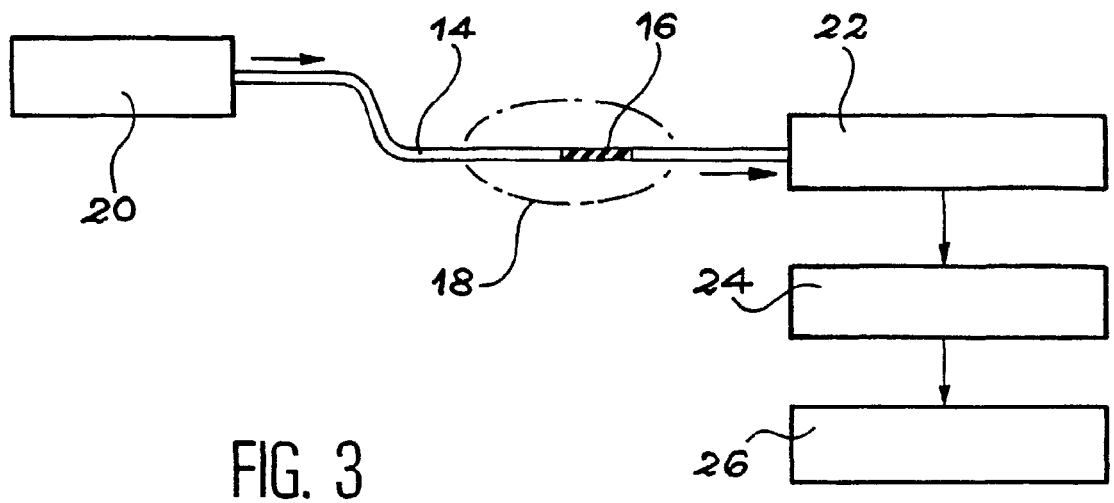
FIGS. 3 to 6 are schematic views of various particular embodiments of the system for measuring refractive indices, which is the subject of the invention.

A first example of the refractive index measurement system, which is the subject of the invention, is schematically shown in FIG. 3 and comprises an optical fibre 14 on which a blazed Bragg grating 16 is formed constituting a transducer.

The protective cladding of the fibre is not shown but it has been removed over the portion of fibre where the grating 16 is formed. This portion of fibre is placed in the medium, the refractive index of which it is desired to measure and which is symbolized by the curve 18.

The system also comprises a broad spectrum optical source 20, the light of which is injected into one end of the optical fibre. This source may be all fibre or not. When it is not all fibre, a means of injecting the light into the fibre is provided.

At the other end of the latter, a spectrum analyser 22, which matches the spectral range covered by the source 20 and the transducer grating 16, is connected.

This spectrum analyser 22 is connected to a digital acquisition device 24 intended to convert the analogue signals provided by the spectrum analyser into digital signals exploitable by an electronic processing device 26 (computer).

The analysis technique described above is implemented (in the form of software) in the electronic processing device 26 which, furthermore, is fitted with means (not shown) for displaying the results provided by the computer.

Figure 4:
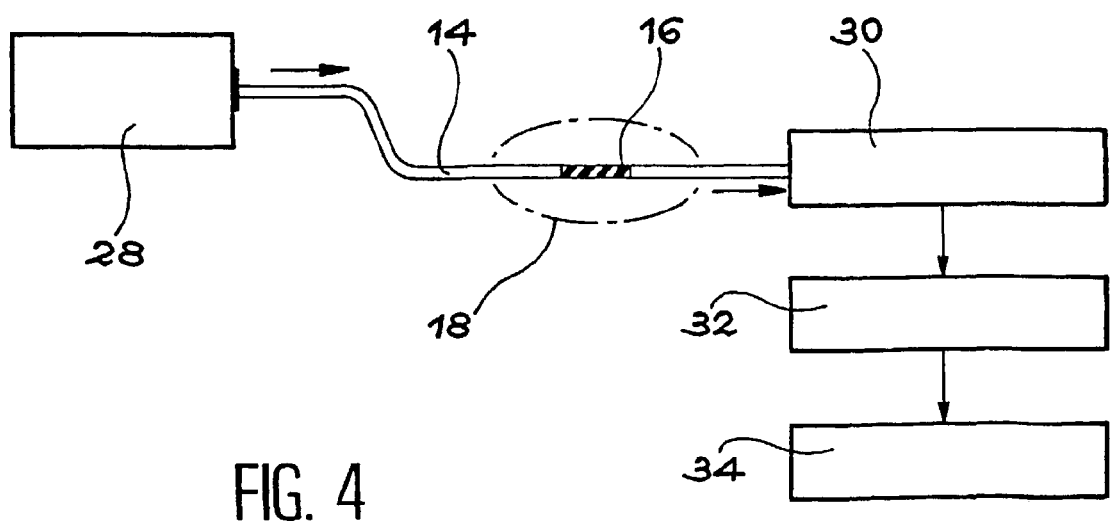

Another example of the system which is the subject of the invention is illustrated schematically in FIG. 4. In this other example, the broad spectrum source 20 is replaced with a laser source 28 with a very narrow spectrum, and which can be spectrally tuned.

In this case, it is no longer necessary to place a spectral analyser at the output of the fibre 14: it is enough to use a single photodetector 30.

Again, the analysis technique mentioned above is employed, by means of an acquisition device 32 connected to the photodetector 30 and a computer 34 connected to the device 32 and provided to employ the technique of analysing the response from the blazed gratings to the refractive index of the external medium.

Figure 5:
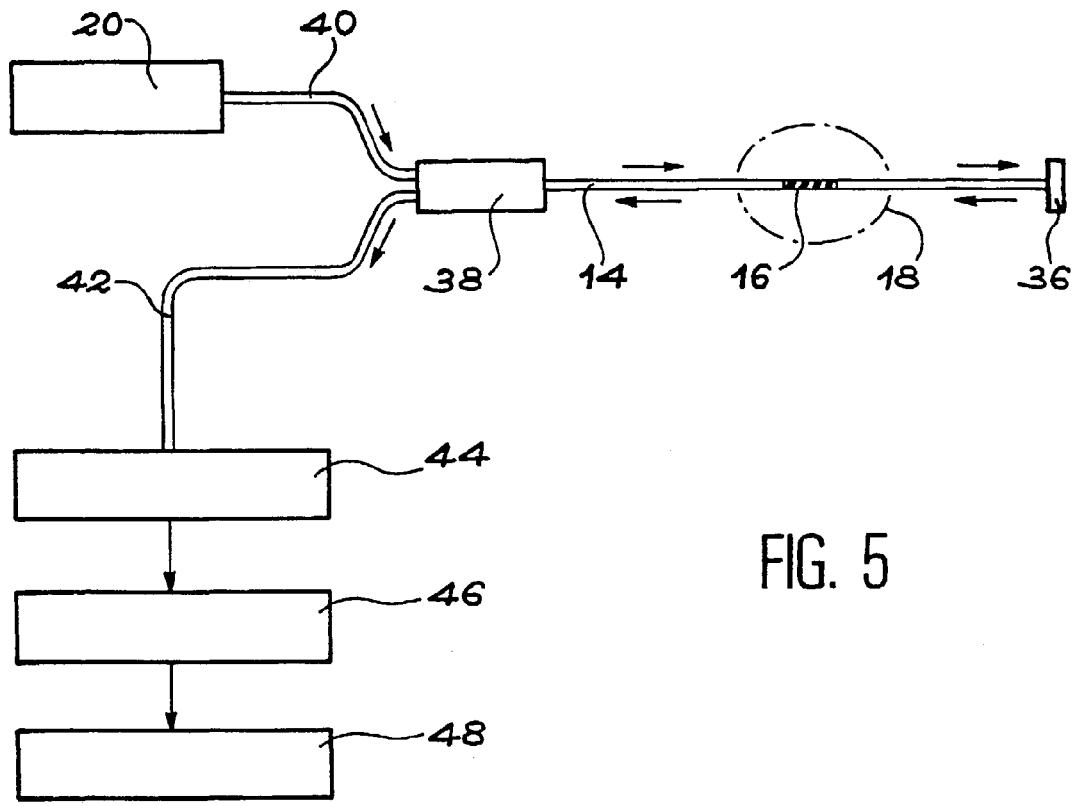

Another example of the system which is the subject of the invention is schematically illustrated in FIG. 5. Unlike the systems of FIGS. 3 and 4 which are operated in transmission, the system of FIG. 5 is operated in reflection. In order to do this, a mirror 36 is placed at one of the ends of the fibre 14.

Advantageously, this mirror 36 is obtained by placing a metal or dielectric coating at this end. The characteristics of this coating depend on the spectral region in which the operation takes place.

An optical coupler 38 of the 1×2 type is connected to the other end of the fibre 14 and, as can be seen, connected via an optical fibre 40 to the broad spectrum light source 20 and, via another optical fibre 42, to a unit for processing light signals successively comprising a spectrum analyser 44, an acquisition device 46 and a computer 48.

The light emitted by the source 20 passes successively through the fibre 40, the coupler 38 and the fibre 14, is reflected on the mirror 36, then passes back through the fibre 14 then through the fibre 42 after having crossed the coupler 38.

The spectrum analyser 44, the acquisition device 46 and the computer 48 cooperate in order to provide measurements of the refractive index of the medium 18 surrounding the portion of fibre which contains the grating 16 while taking account of the fact that, in this case, the operation takes place in reflection.

The person skilled in the art can adapt the example of FIG. 5 to the case where the laser source 28 of FIG. 4, with a very narrow spectrum and which can be spectrally tuned, is used instead of the broad spectrum source 20.

Figure 6:
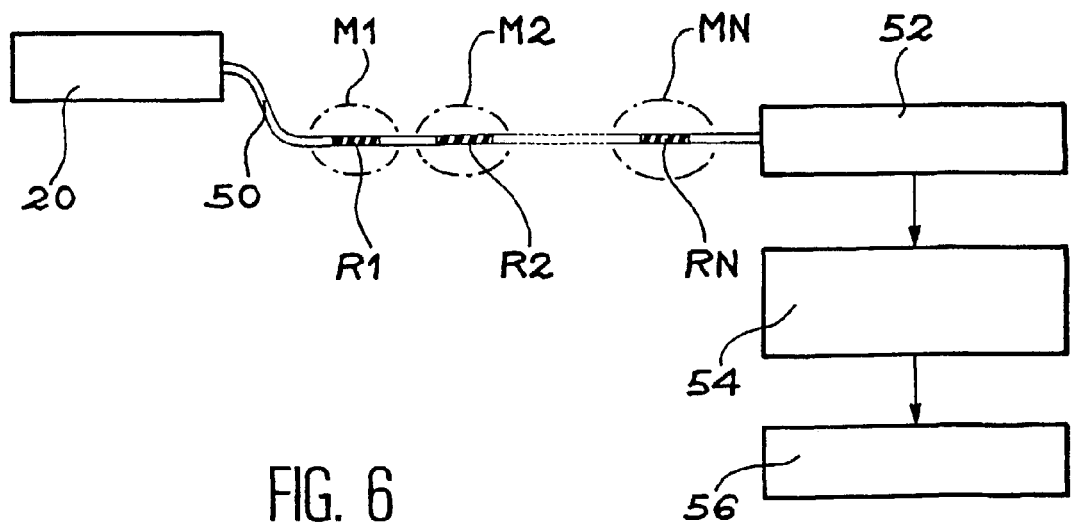

The examples of FIGS. 3 to 5 comprise only a single transducer grating. FIG. 6 illustrates schematically another system according to the invention, operating in transmission, in which a plurality of blazed transducer gratings, for example N gratings R1, R2, . . . , RN, are respectively formed in portions of the same optical fibre 50. The protective cladding on these portions is dispensed with and they are placed in media M1, M2, . . . , MN, respectively, the respective refractive indices of which it is desired to measure.

The broad spectrum light source 20 is again used in the example of FIG. 6 and its light is injected into the fibre 50.

Such a configuration corresponds to a multiplexed system. A spectral region $\Delta\lambda$ ($1 \leq i \leq n$) or channel is allocated specifically to each transducer grating $R_i$. These various channels are demultiplexed (by an electronic, optical or purely digital method) and the refractive index of the medium surrounding each of the gratings is determined.

In order to do this, in the example of FIG. 6, the fibre 50 is again connected to a spectrum analyser 52 provided in order to acquire the transmission spectrum of the set of transducer gratings $R_i$.

This spectrum analyser 52 is connected to an acquisition and demultiplexing device 54 provided in order to transform the analogue signals provided by the spectrum analyser 52 into digital signals and to isolate the spectral region corresponding to each transducer grating.

This acquisition and demultiplexing device 54 is connected to a computer 56 which is fitted with display means (not shown) and which is provided to employ the analysis technique on each of the various spectral regions separated by the acquisition and demultiplexing device 54.

The person skilled in the art can adapt the example of FIG. 6 to operation in reflection, from the example of FIG. 5.

The use of blazed gratings for refractometry has the following advantages:
- a very low sensitivity to temperature and strain (for example much smaller than that
- of the long period gratings),
- a suitable multiplexing capacity,
- a response time of about 1 second, limited only by the computing time of the computer and not by the transducer grating,
- the possibility of adapting the measurement dynamics and the sensitivity by choosing the grating parameters in particularly the blaze angle,
- the possibility of attaining resolutions of about $10^{-5}$, and
- the possibility of making the transducer part operate in reflection.

In addition, it should be noted that the spectral analysis technique of the blazed gratings, explained above, makes it possible to overcome problems of power fluctuation of the light sources or optical sources, of all accidental losses in the blazed grating sensor and of the sensitivity of this sensor, that is to say of the whole intensity transform function of the measurement system. It is a problem that the techniques of the prior art, which are based on an intensity measurement, come up against. It is therefore a determining advantage over the refractometry techniques using evanescent waves.

Moreover, it is not necessary to attack, chemically or mechanically, the initial structure of the waveguide in order to obtain satisfactory sensitivities. It is in fact difficult to control the reproducibility of such processes which furthermore have the major drawback of weakening the waveguide.

This last point is also an advantage to the credit of the present invention with respect to systems using standard Bragg gratings. The latter systems furthermore have a weaker metrological performance (in particular resolutions).

Compared to surface plasmon sensors, the use of blazed gratings allows the simpler use of all-fibre sensors. This is because the manufacturer of a surface plasmon sensor in an optical fibre requires producing a metal coating (typically made of silver) directly on the core of the fibre. It is therefore necessary to remove beforehand the optical cladding of the fibre then to deposit a homogeneous coating right around the latter. Furthermore, technical difficulties in attaching the silver layer to the silica (of which the core of the fibre is generally made), are often encountered.

The technique closest to the present invention is that which uses long period Bragg gratings or LPFG. However, the two types of gratings are very different. Although both produce coupling to the cladding modes of a waveguide, the blazed gratings produce counter directional coupling, connected to much smaller grating periods than those of the LPFG.

Furthermore, instead of analysing a single resonant, the present invention uses all resonants presented by the transmission spectrum of the blazed gratings.

Moreover, the latter are clearly less sensitive to other physical parameters of the external medium such as temperature and strain. This makes it possible to avoid resorting to compensation techniques.

Furthermore, they occupy a smaller spectral range, which improves the multiplexing capacities of the measurement system.

Finally, the lengths of the blazed gratings are less than those of the long period gratings, namely they are about a few millimetres compared to 20 to 30 mm for the LPFG. This makes it possible to make quasi-discrete measurements.

Preferably, the acquisition and spectral analysis means used in the invention are provided in order to acquire each spectrum, with as small a wavelength pitch as allowed by the analysis technique mentioned above.

In addition, the invention can be implemented with waveguides other than the optical fibres, for example with one or more planar waveguides.

The invention claimed is:

1. A system for measuring the refractive index of at least one medium, comprising:
    a waveguide comprising at least one transducer formed by a blazed Bragg grating, in a part of the waveguide brought into contact with a medium, wherein the spectral response of the blazed Bragg grating depends on the refractive index of the medium by means of energy coupling between the guided mode and cladding modes and/or a continuum of radiative modes;
    a light source optically coupled to the waveguide in order to direct light therein and to make the light interact with the grating;
    spectral analysis means for analyzing the light which has interacted with the blazed Bragg grating and for providing a spectrum corresponding to the grating;
    acquisition means for recovering the spectrum; and
    electronic processing means for determining, from the spectrum thus recovered, a value of the refractive index of the medium.

2. The system according to claim 1, wherein the electronic processing means includes means for determining lower and upper envelope curves of the normalized recovered spectrum and a normalized area between the lower and upper envelope curves.

3. The system according to claim 1, wherein the waveguide comprises a single blazed Bragg grating.

4. The system according of claim 1, wherein the waveguide comprises a plurality of blazed Bragg gratings, the spectral analysis means analyzes the light that has interacted with the gratings and to provide the spectra corresponding respectively to the gratings, the acquisition means are provided in order to demultiplex, in an optical or digital manner, the spectra thus provided and to discriminate the respective spectral responses of the gratings, and the electronic processing means are provided in order to correlate the spectral response of each grating with the value of the refractive index of the medium corresponding to the grating.

5. The system according to claim 1, wherein the light source is a broad spectrum source.

6. The system according to claim 3, wherein the light source is a narrow spectrum source, the wavelength of which can be tuned, and the spectral analysis means comprise a photodetector.

7. The system according claim 1, the light source is optically coupled to a first end of the waveguide and the spectral analysis means are optically coupled to a second end of this waveguide, for the purpose of measuring the refractive index by transmission.

8. The system according claim 1, wherein the light source and the spectral analysis means are optically coupled to a first end of the waveguide and means of reflecting the light are provided at the second end of the waveguide, for the purpose of measuring the refractive index by reflection.

9. The system according to claim 1, wherein the acquisition and spectral analysis means are provided in order to acquire each spectrum, with as small a wavelength pitch as allowed by the spectral analysis means.

10. The system according claim 1, the waveguide is an optical fibre.

11. The system according claim 1, the waveguide is a planar waveguide.

* * * * *

UNITED STATES PATENT AND TRADEMARK OFFICE
CERTIFICATE OF CORRECTION

| | | |
|---|---|---|
| PATENT NO. | : 7,184,135 B2 | Page 1 of 1 |
| APPLICATION NO. | : 09/926511 | |
| DATED | : February 27, 2007 | |
| INVENTOR(S) | : Laffont et al. | |

It is certified that error appears in the above-identified patent and that said Letters Patent is hereby corrected as shown below:

On the title page, Item (86), the Filing Date is incorrect. Item (86) should read:

-- (86)  PCT No.:  PCT/IB01/01814

§ 371 (c)(1),
(2), (4) Date:  Nov. 5, 2002 --

Signed and Sealed this

First Day of April, 2008

JON W. DUDAS
*Director of the United States Patent and Trademark Office*